(12) United States Patent
Cho et al.

(10) Patent No.: US 8,214,156 B2
(45) Date of Patent: Jul. 3, 2012

(54) SYSTEM AND METHOD FOR IMPROVING DATA MANAGEMENT BETWEEN IMPLANTABLE MEDICAL DEVICES AND EXTERNAL DEVICES

(75) Inventors: Yong Kyun Cho, Maple Grove, MN (US); Tommy Dean Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 708 days.

(21) Appl. No.: 12/263,430

(22) Filed: Oct. 31, 2008

(65) Prior Publication Data

US 2010/0113895 A1    May 6, 2010

(51) Int. Cl.
*G01N 33/48* (2006.01)
*A61B 5/07* (2006.01)

(52) U.S. Cl. .......................................... 702/19; 600/302
(58) Field of Classification Search ...................... 702/19
See application file for complete search history.

(56) References Cited

U.S. PATENT DOCUMENTS

| | | | |
|---|---|---|---|
| 5,720,771 A | 2/1998 | Snell | |
| 6,129,746 A | 10/2000 | Levine et al. | |
| 6,507,759 B1 | 1/2003 | Prutchi et al. | |
| 2004/0172080 A1 | 9/2004 | Stadler et al. | |
| 2005/0080460 A1 | 4/2005 | Wang et al. | |
| 2005/0137636 A1 | 6/2005 | Gunderson et al. | |
| 2006/0017575 A1 | 1/2006 | McAdams | |
| 2006/0017576 A1 | 1/2006 | Gordon et al. | |
| 2006/0089684 A1 | 4/2006 | Blaha et al. | |
| 2006/0224079 A1 | 10/2006 | Washchuk | |
| 2006/0247706 A1 | 11/2006 | Germanson et al. | |
| 2008/0024293 A1 | 1/2008 | Stylos | |

OTHER PUBLICATIONS (PCT/US2009/060743) PCT Notification of Transmittal of the International Search Report and the Written Opinion of the International Searching Authority, 13 pages, mailed May 18, 2010.

*Primary Examiner* — Jerry Lin (57) ABSTRACT

Systems, methods and devices are provided for improving data management between implantable medical devices (IMDs) and external devices for the detection of volume overload and volume depletion conditions. Data acquired by the IMD is periodically communicated to the external device where a volume overload monitoring algorithm is operated to detect whether a volume overload condition is present in the patient by monitoring the acquired data at the external device at a first lower, non-real-time frequency rate. Upon detection of a volume overload condition, the external device issues an instruction to the IMD causing the IMD to initiate a volume depletion condition monitoring algorithm for detecting in real time whether a volume depletion condition is present in the patient.

15 Claims, 5 Drawing Sheets

SYSTEM AND METHOD FOR IMPROVING DATA MANAGEMENT BETWEEN IMPLANTABLE MEDICAL DEVICES AND EXTERNAL DEVICES

TECHNICAL FIELD

This disclosure relates generally to medical devices and more particularly to a system and method for improving data management between implantable medical devices (IMDs) and external devices by means of wireless communications between the devices.

BACKGROUND

Patients having such conditions as heart failure or decreased kidney function requiring dialysis often have undesirable fluid accumulation in the body. In general, fluid accumulation is a failure or over-response of the homeostatic process within the body. The body normally prevents the build up of fluids by maintaining adequate pressures and concentrations of salt and proteins and by actively removing excess fluid. Fluid accumulation can occur, for example, when the body's mechanisms for preventing fluid accumulation are affected by disease, such as heart failure, left sided myocardial infarction, high blood pressure, altitude sickness, emphysema (all which affect pressures), cancers that affect the lymphatic system, kidney failure, and diseases that disrupt the protein concentrations. As a result, providing an adequate monitor of the patient's fluid status can provide physicians and patients with a better tool to manage disease.

Patients with conditions that contribute to fluid accumulation in the body often regulate the level of accumulated fluid through the use of diuretics. This can be a delicate balancing act, since fluid accumulation can result in frequent and lengthy hospitalization and overuse of diuretics or other fluid reduction tools can result in dehydration. In some case, dehydration may become so severe as to result in hypovolaemic shock, including: diminished consciousness, lack of urine output, cool moist extremities, a rapid and feeble pulse (the radial pulse may be undetectable), low or undetectable blood pressure, and peripheral cyanosis.

SUMMARY

Systems, methods and devices are described herein for improving data management between implantable medical devices (IMDs) and external devices by means of wireless communications between the devices for the detection of certain medical conditions in a patient in which an IMD is implanted. In one or more embodiments, an IMD is configured for acquiring data related to at least one parameter sensed within a patient useful in detecting medical conditions, symptoms or events in a patient. The acquired data is periodically communicated from the IMD to an external device for further processing and/or analysis. A first medical condition monitoring algorithm is operated at the external device for monitoring the acquired data at the external device at a first lower, non-real-time frequency rate to detect a first medical condition, such as volume overload, in the patient that typically does not fluctuate or change rapidly within the patient. Upon detecting the first medical condition (i.e., volume overload), the external device issues an instruction or command to the IMD causing the IMD to initiate a second medical condition monitoring algorithm for monitoring data related to a second medical condition, such as volume depletion, at a second higher frequency rate to detect a second medical condition that typically may occur, fluctuate or change rapidly in the patient. In one or more embodiments, the second higher frequency rate monitors data in substantially real-time to when the monitored data is acquired to detect volume depletion in the patient while the first lower frequency rate is in non-real-time to when to the monitored data is acquired such that volume overload is monitored in non-real-time. In one or more embodiments, upon detection of either volume overload or volume depletion, an alert may be generated to notify a patient, a clinician or another individual or device or the detected condition. In one or more embodiments, significant processing and power in the IMD can be conserved by only monitoring for volume depletion in the patient upon the detection of volume overload by an external device.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, mechanical, electrical, functional, and other changes may be made without departing from the scope of the present disclosure. The following detailed description is, therefore, not to be taken in a limiting sense, and the scope of the present disclosure is defined only by the appended claims.

Fluid Accumulation ("volume overload" or "VO") and dehydration ("volume depletion" or "VD") have been monitored using external thoracic impedance measurements and internal thoracic impedance measurement. Also, these events can be monitored and detected using intracardiac pressure measurements. These measurements have been used to simply monitor the condition or to indicate the need for intervention such as the use of diuretics or dialysis. Because thoracic fluid levels change based on body position and other external influences, measurements often had to be taken at various times of the day (i.e., nighttime or at rest and daytime or active) and averaged or otherwise manipulated to understand the true fluid level in the patient.

It is believed that volume overload typically develops over a longer period of time than volume depletion. Abrupt onset edema or volume overload is possible, but it is an exception to the general rule. It is also believed that most dangerous instances of volume depletion occur as a result of an excessive response to an incident of volume overload. The treatment of a volume overload condition can require a precise dosage of diuretic, and the consequence of an excessive dose can often be a severe or even dangerous volume depletion condition.

Certain embodiments of the invention include an implantable medical device (IMD) capable of monitoring volume overload ("VO") and volume depletion ("VD") events occurring in a patient. Systems, devices and methods for detecting VO and VD are disclosed in U.S. Pat. No. 7,963,922 B2 entitled "Volume Depletion Detection" filed on Apr. 28, 2006, the contents of which are hereby incorporated by reference it its entirety.

Various embodiments will be described herein as being implemented in implantable medical devices (IMDs) that include sensing capabilities for monitoring physiological conditions and parameters and acquiring data related thereto. An IMD in which the invention is implemented may be primarily intended for detecting heart-related conditions (e.g., volume overload, volume depletion, etc.) or may primarily be intended for other purposes. For example, the IMD may comprise any type of implanted device including, but not limited to cardiac pacemakers, implantable cardioverter-defibrillators (ICDs), implantable combination pacemaker-cardioverter-defibrillator (PCDs), implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

A wide variety of IMDs have been developed in order to monitor patient conditions and deliver therapy to the patient. An IMD typically includes a hermetically sealed housing coupled to one or more leads that are surgically implanted inside a patient for sensing conditions or for administering therapy. The IMD includes sensing or monitoring capabilities. For example, the IMD may sense information within a patient and store the sensed information for subsequent analysis. Alternatively or additionally, the IMD may provide therapeutic stimulation to the patient or may deliver drugs or agents to the patient. In some cases, the sensed information may be used directly by the IMD to adjust or control the therapy that is delivered to the patent. Telemetry is used to communicate sensed information from the IMD to an external device so that analysis of the sensed information can be performed. Telemetry is further used to communicate information or instructions from external devices to the IMD.

Figure 1:
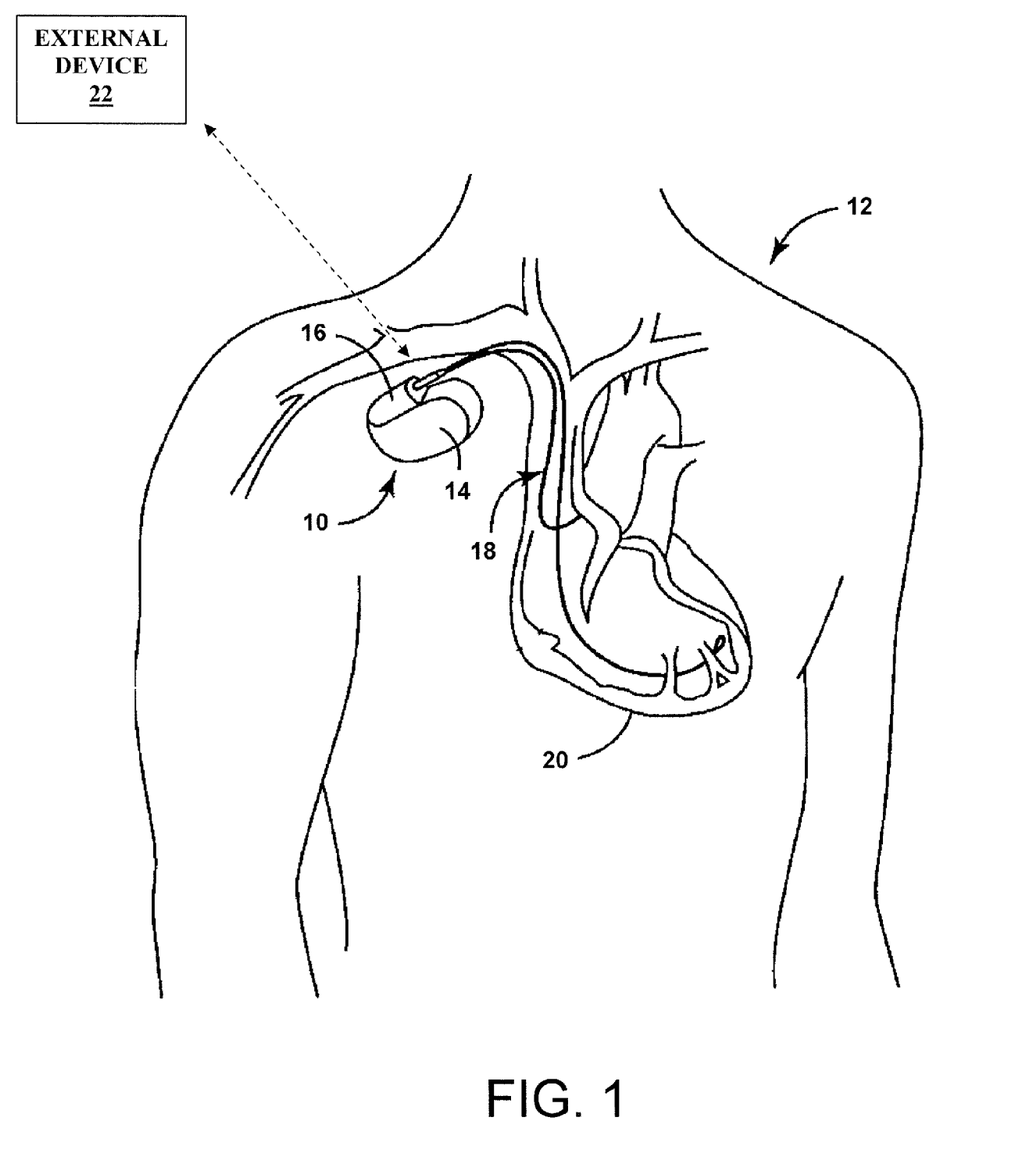
FIG. 1 illustrates components of the system including an implantable medical device in accordance with one or more embodiments of the present disclosure.

Referring now to FIG. 1, a schematic representation of an implantable medical device (IMD) 10 that may be used in accordance with certain embodiments of the invention is illustrated as being implanted within a patient 12. In one or more embodiments, the system includes an IMD 10 in wireless telemetry communication with an external device 22. In one or more embodiments, IMD 10 may comprise a hermetically sealed enclosure 14 and connector module 16 for coupling IMD 10 to electrical leads and other physiological sensors arranged within body 12, such as pacing and sensing leads 18 connected to portions of heart 20 for delivery of pacing pulses to heart 20 of patient 12 and sensing at least one physiological parameter within heart 20. While IMD 10 is depicted in a pacemaker device configuration in FIG. 1, it is understood that IMD 10 may comprise any type of implanted, subcutaneous or external medial device. IMD 10 may collect and process data from one or more sensors for deriving parameters used in computing a probability that a medical condition is occurring in patient 12 in which IMD 10 is implanted.

Figure 2:
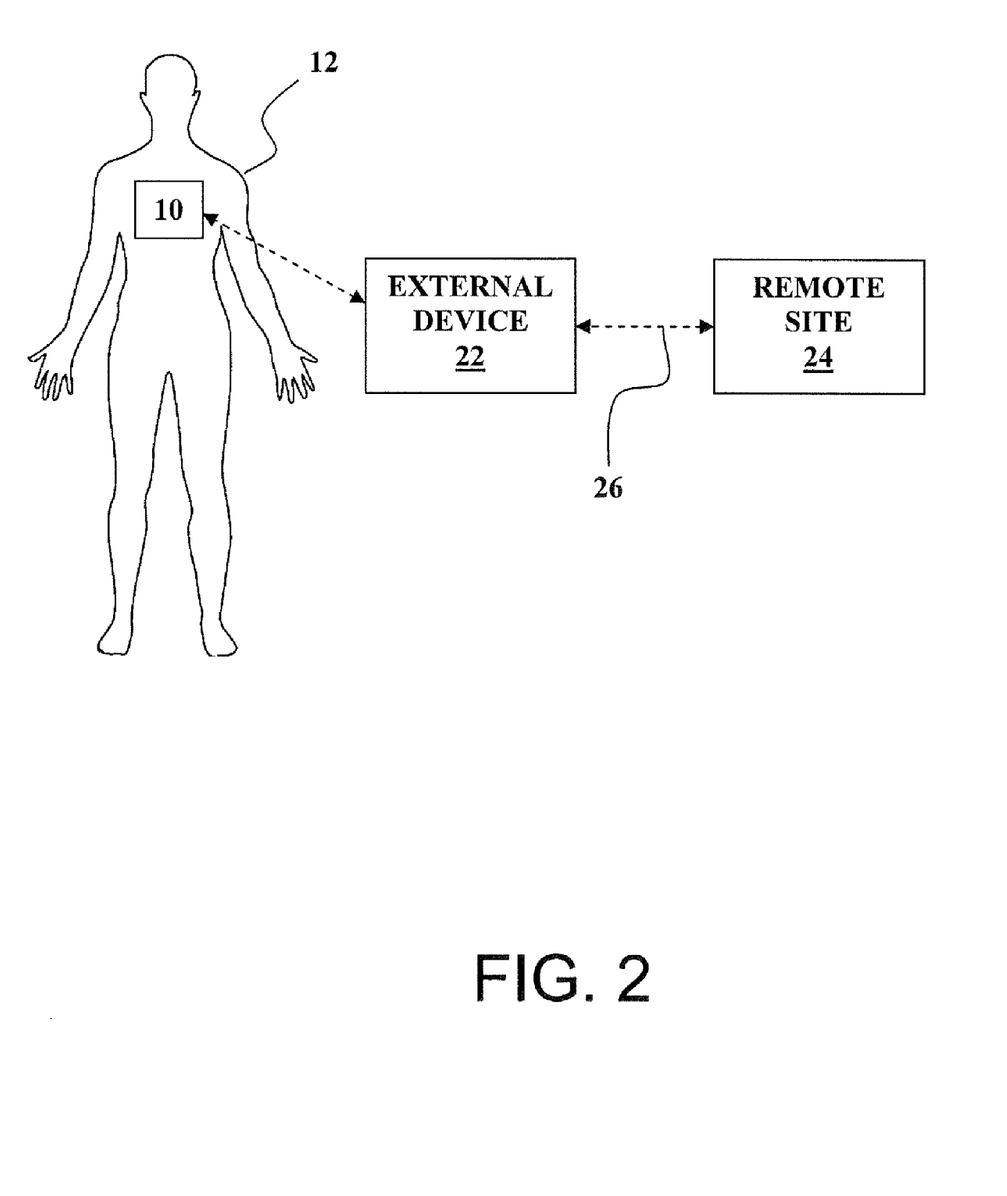
FIG. 2 illustrates components of the system including an implantable medical device in accordance with one or more embodiments of the present disclosure.

In one or more embodiments, external device 22 may comprise an external medical device, a programming device, a remote telemetry station, a physician-activated device, a patient-activated device, a mobile handheld unit (e.g., mobile phone, PDA, etc.), a personal computer, an in-home monitoring device, a patient-wearable device, a display device or any other type of device capable of sending and receiving signals to and from IMD 10. In one or more embodiments, external device 22 may comprise an in-home monitoring device, such as the Medtronic CareLink® Network monitor, that collects information from IMDs implanted in patients and communicates such information to a remote site 24 (e.g., remote clinicians, remote devices or the like) through a connection 26, such as the Internet, phone lines or wireless networks, as illustrated in FIG. 2. Carelink is a registered trademark of Medtronic, Inc. of Minneapolis, Minn. In one or more embodiments, external device 22 may comprise a personal computer or mobile phone having a software program installed thereon configured for receiving data from IMD 10, processing such data and/or further communicating such data to a remote location or clinician for further analysis and/or processing.

Communication between IMD 10 and external device 22 can occur via telemetry, such as a long-distance telemetry system through an RF telemetry module that facilitates wireless data transfer between IMD 10 and external device 22. The devices may be configured to perform any type of wireless communication, such as but not limited to radio frequency (RF) signals, infrared (IR) frequency signals, or other electromagnetic signals. Any of a variety of modulation techniques may be used to modulate data on a respective electromagnetic carrier wave. Alternatively, sound waves may be used for communicating data or the patient's tissue may be as the transmission medium for communicating with a programmer positioned on the patients skin. Other types of wired communications may also occur when IMD 10 is alternatively configured as an external device or contains wired communication channels that extend from within the patient to points outside of the patient.

IMDs typically must rely entirely on an implanted power source. It is desirous to keep the physical size of an IMD to a minimum, which further places limitations on the size of the implanted power source. The various internal electrical components of IMD 10 (e.g., controllers, memory, sensors, RF telemetry modules, etc.) rely on this limited power source for power. For embodiments of IMD 10 that have nonrechargeable batteries, IMD 10 must be surgically replaced when the power source is fully depleted. For embodiments of IMD 10 having rechargeable batteries, a surgical procedure is not required when the power source is depleted, however, the power source typically must be recharged more frequently since it cannot store as much energy. Thus, power conservation is particularly important in IMD 10. Further, consistently powering up components of IMD 10 to monitor possible medical conditions occurring in a patient require electrical power and computational processing which can drain the battery of IMD 10 at an unacceptable rate. Still further, the processing capabilities of IMD 10 are also typically limited by the intention to keep the physical size of an IMD to a minimum. Thus, in various embodiments described herein, substantial data processing is moved to the external device 22, which are much more flexible in their complexity and computational speed as they are not restricted by the same restrictions facing IMD-based algorithms and components. However, external computer-based algorithms being performed by external device 22 are only effective when there is sufficient transmission of data relating to sensed parameters within the patient from IMD 10 to external device. Systems, methods and devices are described herein for improving data management between IMD 10 and external device 22 by means of wireless communications between the devices for the detection of certain medical conditions in a patient 12 in which an IMD 10 is implanted.

Figure 3:
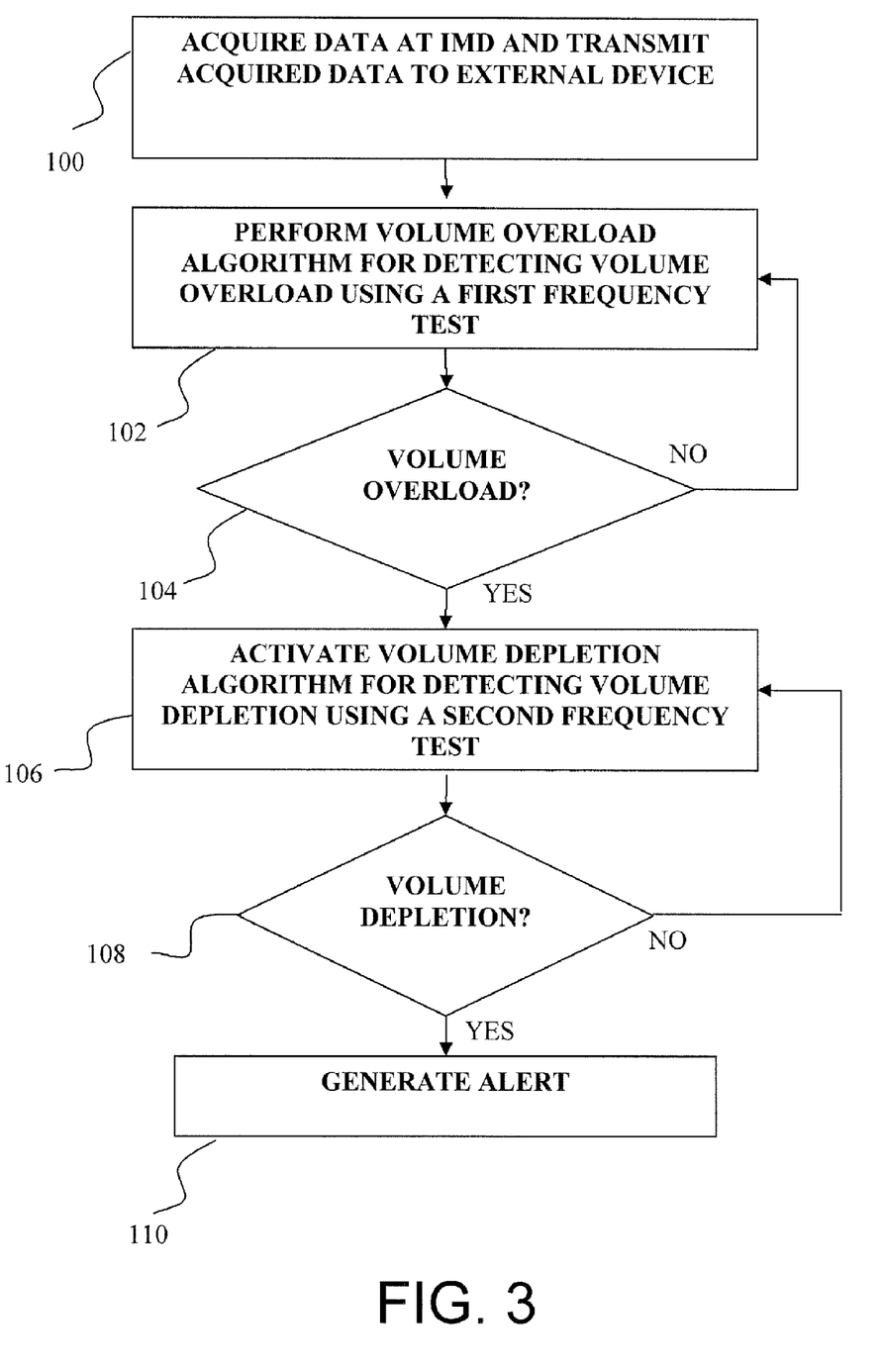
FIG. 3 is an operational flow diagram illustrating a process for detecting volume overload and volume depletion in a patient in accordance with one or more embodiments of the present disclosure.

Referring now to FIG. 3, an operational flow diagram is illustrated in accordance with one or more embodiments of the present disclosure for detecting VO and/or VD in a patient 12. Initially, IMD 10 is configured for acquiring data related to at least one parameter sensed within a patient useful in detecting volume overload in a patient 12 in operation 100, wherein the acquired data is periodically communicated from IMD 10 to external device 22 for further processing and/or analysis. Since it is believed that volume overload typically develops over a long period of time and does not involve rapid onset or changes, it is possible to periodically monitor for volume overload using post-processing (i.e., non-real-time processing) of data that is periodically transmitted from IMD 10 to external device 22. Thus, external device 22 performs a volume overload monitoring algorithm in operation 102 for monitoring the acquired data at external device 22 at a first lower, non-real-time frequency rate to detect for indications that volume overload is occurring in the patient 12. If no volume overload is detected in operation 104, then external device 22 continues to periodically monitor data as it is received for volume overload conditions.

If volume overload is detected from the monitored data in operation 104, then external device 22 issues an instruction or command to IMD 10 that causes IMD 10 to initiate a volume depletion monitoring algorithm in operation 106 for acquiring and monitoring data related to volume depletion at a second higher frequency rate to detect whether volume depletion is occurring in the patient 12. Since the treatment of a volume overload condition often requires a precise dosage of diuretic, and the consequence of an excessive dose of the same can often be a severe or even dangerous volume depletion condition, the initiation of monitoring for volume depletion can be withheld until after volume overload has been detected by external device 22. further, since volume depletion is more susceptible to an abrupt onset, monitoring of volume depletion is preferably performed by IMD 10 in substantially real-time to when the monitored data is acquired by IMD 10. This allows volume depletion to be detected in substantially real-time to when it may be occurring in a patient, while also conserving processing and power in IMD 10 until those points in time when volume depletion is more likely to be occurring in the patient 12.

If volume depletion is detected by the volume depletion monitoring algorithm in operation 108, then an alert may be generated in operation 110 to notify the patient, a clinician or another individual or device at the remote site 26 of the detected volume depletion condition. Similarly, the alert my provide an indication of either the detected volume overload condition or other relevant conditions.

Figure 4:
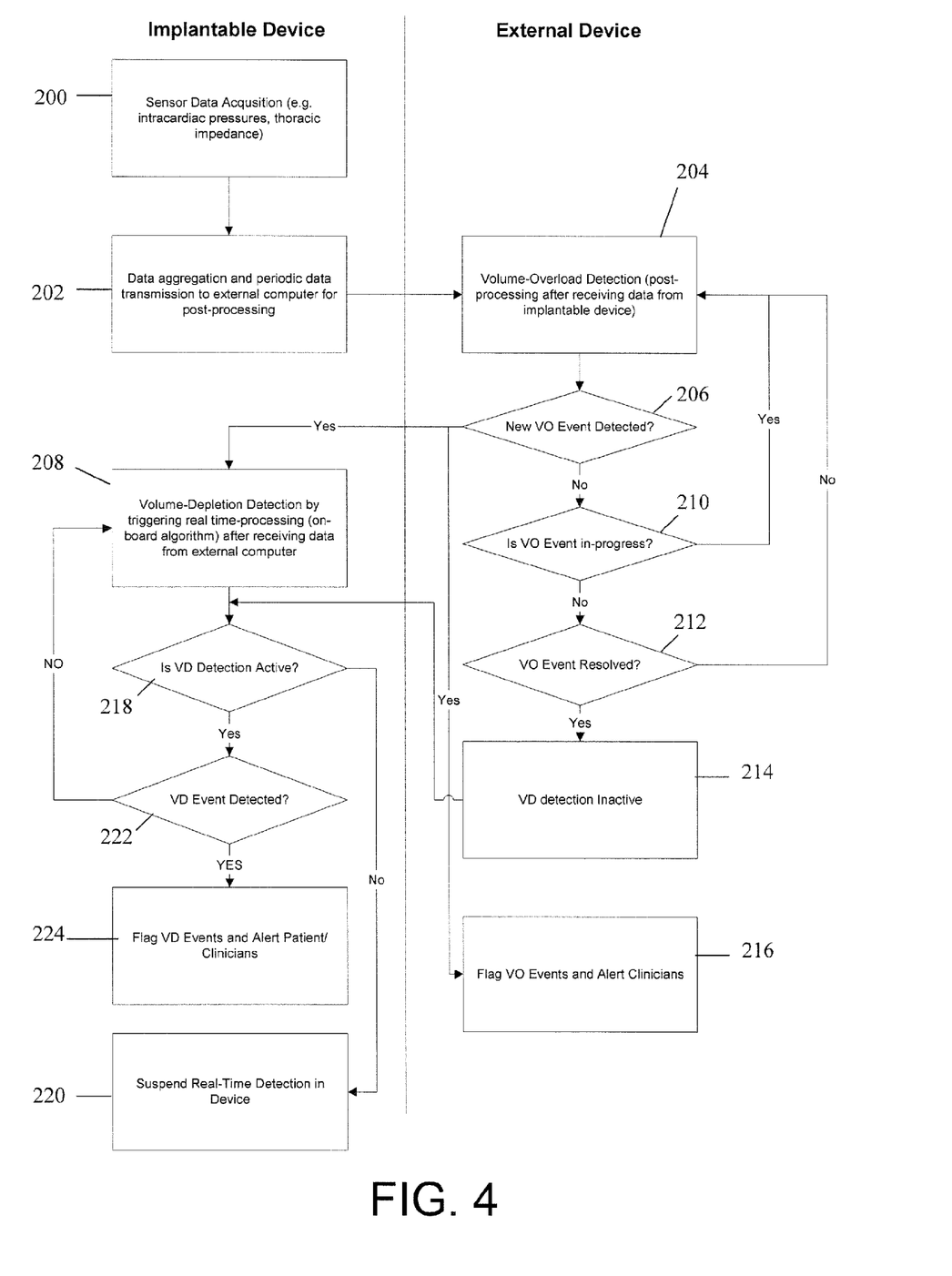
FIG. 4 is an operational flow diagram illustrating a process for detecting volume overload and volume depletion in a patient in accordance with one or more embodiments of the present disclosure.

Referring now to FIG. 4, a more detailed operational flow diagram is illustrated in accordance with one or more embodiments showing a more detailed description of the various separate algorithms being implemented by IMD 10 and external device 22 and their interaction. Initially, sensors connected to IMD 10 are configured for acquiring data related to at least one parameter sensed within a patient useful in detecting volume overload in a patient 12 in operation 200 (e.g., intracardiac pressures, thoracic impedance, etc.), wherein the sensed data is acquired and aggregated in the memory of IMD 10 and periodically communicated from IMD 10 to external device 22 for further processing and/or analysis in operation 202. External device 22 performs the volume overload monitoring algorithm in operation 204 for performing post-processing (i.e., non-real-time) of the acquired data at external device 22 at a first lower, non-real-time frequency rate to detect for indications that volume overload is occurring in the patient 12. If a new volume overload condition is detected in operation 206, then external device 22 issues an instruction or command to IMD 10 that causes IMD 10 to initiate a volume depletion monitoring algorithm in operation 208 for acquiring and monitoring data related to volume depletion at a second higher frequency rate to detect whether volume depletion is occurring in the patient 12.

In one or more embodiments, if a new volume overload condition is not detected from the monitored data in operation 206, then it is determined in operation 210 whether a volume overload condition previously detected is still in progress. If so, the volume overload monitoring algorithm returns to operation 204 to continue to periodically monitor the data external device 22 receives from IMD 10 for continued volume overload conditions. If a previously detected volume overload condition is not still in progress, it is determined in operation 212 whether such previously detected volume overload condition has been resolved. If not, the volume overload monitoring algorithm returns to operation 204 to continue to periodically monitor the data external device 22 receives from IMD 10 for continued volume overload conditions. If the previously detected volume overload condition has been resolved, then the volume overload monitoring algorithm is inactivated in operation 214. Further, once any volume overload conditions are resolved, the volume depletion monitoring algorithm is also inactivated in operation 214 (e.g., VD detection is flagged or marked as inactive) and IMD 10 is notified of the inactivation of the volume depletion monitoring algorithm, for subsequent use by IMD 10 when determining if the volume depletion monitoring algorithm is active in operation 218, In one or more embodiments, when the new volume overload event is detected in operation 206, then a volume overload event can be flagged in external device in operation 216 and an alert may be generated to notify the patient, a clinician or another individual or device at the remote site 26 of the detected volume overload condition.

After instructing IMD 10 of the detected volume overload condition, IMD 10 initiates the volume depletion monitoring algorithm in operation 208 for acquiring and monitoring data related to volume depletion at a second higher frequency rate to detect whether volume depletion is occurring in the patient 12. In one or more embodiments, monitoring of volume depletion is preferably performed by IMD 10 in substantially real-time to when the monitored data is newly acquired by IMD 10 to allow volume depletion to be detected in substantially real-time to when it may be occurring in the patient. In operation 218, it is determined if the volume depletion monitoring algorithm is actively running in IMD 10. If the volume depletion monitoring algorithm has been inactivated and should not be active, then real-time detection of volume depletion is suspended in IMD 10 in operation 220. In some embodiments, the volume depletion monitoring algorithm can be inactivated in response to any inactivation commands received by IMD 10 as output by external device 22 in response to operation 214. In some embodiments, the volume depletion monitoring algorithm can be inactivated in response to other factors or conditions, such as after a VO event has been determined to have been resolved or after a certain amount of time after a VO event has been determined to have been resolved (e.g., VO event resolution+N days, where N is selected number of days).

If the volume depletion monitoring algorithm is active, then it is determined in operation 222 if the volume depletion-related data that is acquired and monitored at a second higher frequency rate (i.e., real-time) indicates whether volume depletion is occurring in the patient 12. If not, the volume depletion monitoring algorithm returns to operation 208 to continue to periodically monitor the data that IMD 10 acquires to detect volume depletion conditions. If a volume depletion condition is detected, then a volume depletion event can be flagged in IMD 10 in operation 224 and an alert may be generated to notify the patient, a clinician or another individual or device at the remote site 26 of the detected volume overload condition.

Figure 5:
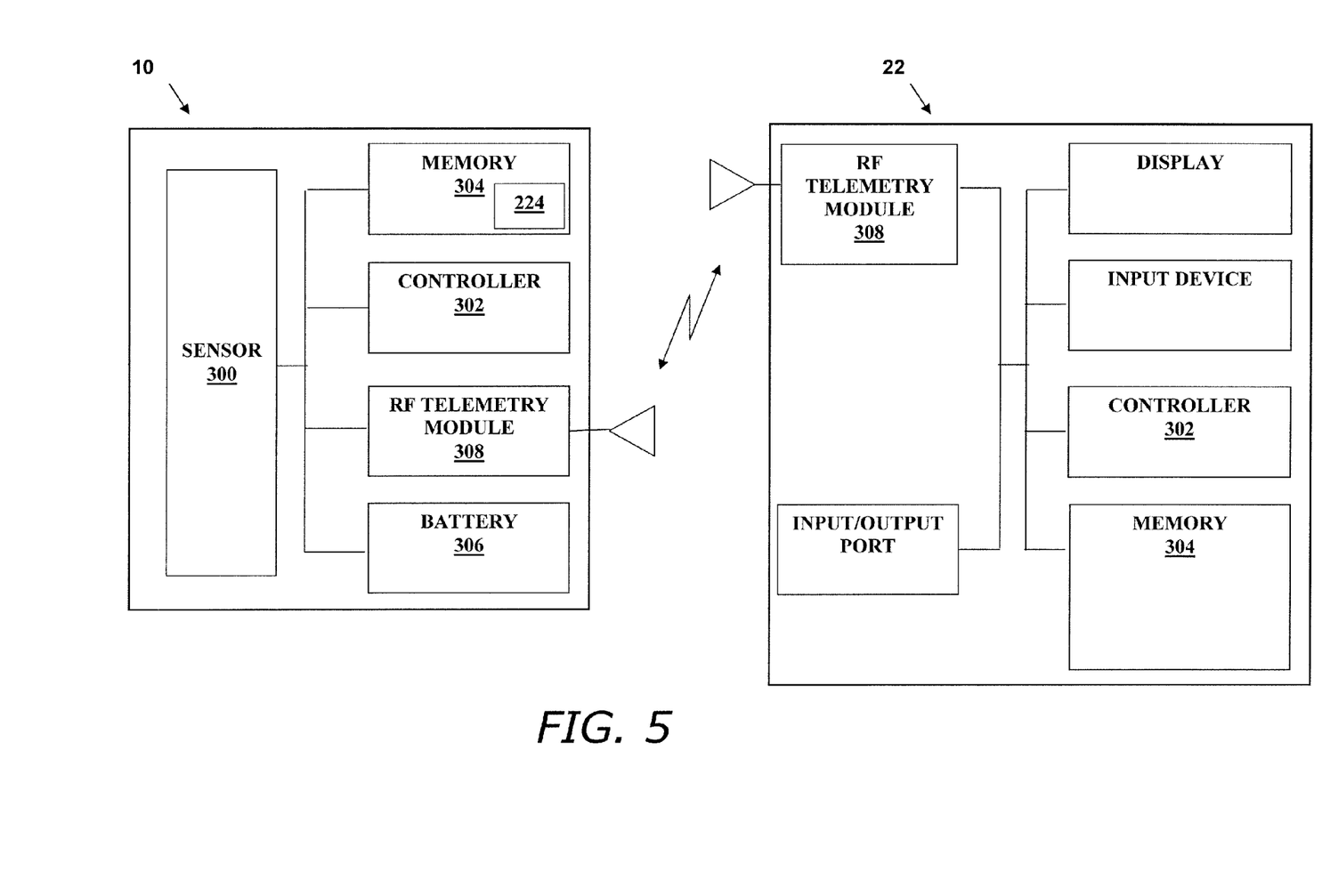
FIG. 5 is a block diagram illustrating the various system components including an implantable medical device and an external device in accordance with one or more embodiments of the present disclosure.

With reference to FIG. 5, a block diagram is provided illustrating the various system components included within IMD 10 and external device 22 in accordance with one or more embodiments of the present disclosure. IMD 10 is shown as including at least one sensor 300, controller 302 or processor, memory 304, battery 306, RF telemetry module 308, therapy module 310, and other components as appropriate to produce the desired functionalities of the device.

In one or more embodiments, sensor 300 may be configured to sense at least one physiological parameter within patient 12 associated with the detection of volume depletion or volume overload. In one or more embodiments, data obtained by sensor 300 may be provided to controller 302, which suitably analyzes the data, stores appropriate data in memory 304, or provides a response or report as appropriate. In one or more embodiments, controller 302 may be configured to operate control algorithms and the volume depletion monitoring algorithm stored in memory 304. Controller 302 may be implemented with any type of microprocessor, digital signal processor, application specific integrated circuit (ASIC), field programmable gate array (FPGA) or other integrated or discrete logic circuitry programmed or otherwise configured to provide functionality as described herein. Controller 302 executes instructions stored in memory 304 to provide functionality as described herein for IMD 10. Instructions provided to controller 302 may be executed in any manner, using any data structures, architecture, programming language and/or other techniques. Memory 304 is any storage medium capable of maintaining digital data and instructions provided to controller 302 such as a static or dynamic random access memory (RAM), read-only memory (ROM), non-volatile random access memory (NVRAM), electrically erasable programmable read-only memory (EEPROM), flash memory, or any other electronic, magnetic, optical or other storage medium.

Similarly, external device 22 includes a corresponding controller 302 or processor, memory 304, power source 306, RF telemetry module 308, and other components as appropriate to produce the desired functionalities of the device. In one or more embodiments, controller 302 in external device 22 may be configured to operate control algorithms and the volume overload monitoring algorithm stored in memory 304 of external device 22.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method comprising:
acquiring data in an implantable medical device (IMD) related to detecting volume overload within a patient and periodically communicating the acquired data to an external device;
performing a volume overload monitoring algorithm in the external device for monitoring the acquired data at the external device at a first lower frequency rate to detect volume overload in the patient;
upon detecting volume overload, causing the IMD to initiate a volume depletion monitoring algorithm for monitoring data related to volume depletion at a second higher frequency rate.

2. The method of claim 1, wherein the second higher frequency rate monitors data in substantially real-time to when the monitored data is acquired while the first lower frequency rate is in non-real-time to when to the monitored data is acquired.

3. The method of claim 1, further comprising communicating an instruction from the external device to the IMD upon detection of volume overload instructing the IMD to a volume depletion monitoring algorithm.

4. The method of claim 1, further comprising generating an alert to at least one of a patient and a clinician upon detection of volume depletion.

5. The method of claim 1, further comprising acquiring data required for monitoring the first medical condition at a sampling rate of a lower frequency than a sampling rate at which data is acquired for monitoring volume depletion.

6. A system for detecting volume depletion in a patient comprising:
an implantable medical device (IMD) configured for acquiring data related to sensed physiological parameters within a patient associated with volume overload and for periodically communicating the acquired data to an external device;
an external device configured for:
performing a volume overload monitoring algorithm for monitoring the acquired data at the external device at a first lower frequency rate to detect volume overload in the patient; and
upon detecting volume overload in the patient, generating an instruction to the IMD to monitor for volume depletion in the patient; and
wherein the IMD is further configured for initiating a volume depletion monitoring algorithm for monitoring data related to volume depletion at a second higher frequency rate to detect volume depletion in the patient 7. The system of claim 6, wherein the IMD is configured to monitor for volume depletion in substantially real-time to when the monitored data is acquired while the external device is configured to monitor for volume overload in non-real-time to when to the monitored data is acquired.

8. The system of claim 6, wherein the IMD is configured to generate an alert to at least one of a patient and a clinician upon detection of volume depletion.

9. The system of claim 6, wherein the external device is configured to generate an alert to at least one of a patient and a clinician upon detection of volume overload.

10. The system of claim 6, wherein the IMD is configured for acquiring data required for monitoring volume overload at a less frequent data sampling rate than a sampling rate at which data is acquired for monitoring volume depletion.

11. A system comprising:
- means for acquiring data in an implantable medical device (IMD) related to detecting volume overload within a patient and periodically communicating the acquired data to an external device;
- means for performing a volume overload algorithm in the external device for monitoring the acquired data at the external device at a first lower frequency rate to detect volume overload in the patient;
- means for instructing the IMD to monitor for volume depletion in the patient upon detecting volume overload; and
- means for performing a volume depletion monitoring algorithm in the IMD upon receipt of the instruction at the IMD for monitoring data related to volume depletion at a second higher frequency rate.

12. The system of claim 11, wherein the means for performing the volume depletion monitoring algorithm monitors for volume depletion in substantially real-time to when the monitored data is acquired while the means for performing the volume overload algorithm monitors for volume overload in non-real-time to when to the monitored data is acquired.

13. The system of claim 11, further comprising means for generating an alert from the IMD to at least one of a patient and a clinician upon detection of volume depletion.

14. The system of claim 11, further comprising means for generating an alert from the external device to at least one of a patient and a clinician upon detection of volume overload.

15. The system of claim 11, wherein the means for acquiring data in the IMD is configured for acquiring data required for monitoring volume overload at a less frequent data sampling rate than a sampling rate at which data is acquired for monitoring volume depletion.

* * * * *